(12) United States Patent
Crabb et al.

(10) Patent No.: US 10,023,617 B1
(45) Date of Patent: Jul. 17, 2018

(54) METHODS AND SYSTEMS OF PRODUCING PHARMACEUTICAL GRADE LANTIBIOTICS

(71) Applicant: ImmuCell Corporation, Portland, ME (US)

(72) Inventors: Joseph H. Crabb, Portland, ME (US); John W. Zinckgraf, Portland, ME (US); Hanna Froebe, Portland, ME (US)

(73) Assignee: ImmuCell Corporation, Portland, ME (US)

( * ) Notice: Subject to any disclaimer, the term of this patent is extended or adjusted under 35 U.S.C. 154(b) by 0 days.

(21) Appl. No.: 15/868,765

(22) Filed: Jan. 11, 2018

(51) Int. Cl.
C07K 14/315 (2006.01)
C12N 1/20 (2006.01)
A61K 38/00 (2006.01)

(52) U.S. Cl.
CPC .............. *C07K 14/315* (2013.01); *C12N 1/20* (2013.01); *A61K 38/00* (2013.01)

(58) Field of Classification Search
None
See application file for complete search history.

(56) References Cited

PUBLICATIONS

Gonzalez-Toledo et al (J. Food Sci., 75:M347-M353, 2010).*
Guerra et al (Int. J. Food Microbiol., 70:267-281, 2001).*

* cited by examiner

*Primary Examiner* — Brian J Gangle
(74) *Attorney, Agent, or Firm* — Polsinelli PC

(57) ABSTRACT

Methods and systems for efficient and cost-effective production of lantibiotics. The methods and systems are capable of producing lantibiotics having high purity suitable for pharmaceutical use.

21 Claims, No Drawings

US 10,023,617 B1

METHODS AND SYSTEMS OF PRODUCING PHARMACEUTICAL GRADE LANTIBIOTICS

FIELD OF THE INVENTION

The present disclosure relates to methods and systems for efficient and cost-effective production of lantibiotics. The methods and systems are capable of producing lantibiotics having high purity suitable for pharmaceutical use.

BACKGROUND OF THE INVENTION

Resistance of bacteria to conventional antibiotics used to treat human disease has risen to an international crisis level. A contributing factor has been the widespread use of antibiotics to treat non-life-threatening infections. In recent years, there has been much focus on a promising new class of bacteriocins known as lantibiotics. At present, lantibiotics are being used extensively by the food industry. Lantibiotics have significant commercial value and broad applicability, and practical methods for their production would have a significant economic impact.

Lantibiotics are antimicrobial proteins produced by bacteria that display growth-inhibitory activity against a range of related bacteria. Lantibiotics are polypeptide antimicrobial agents that are produced by certain bacteria and are distinguishable from other antibiotics because of their polypeptide nature and bioactive properties. For example, nisin, a lysine-rich lantibiotic used as a preservative for certain foods, has the unusual amino acid residues lanthionine and β-methyl-lanthionine. Nisin is non-toxic to humans and animals, is resistant to high temperatures, and is bacteriostatic at very low concentrations. Unfortunately, although lantibiotics are versatile and have unique and advantageous properties, the lack of commercially viable methods for production and isolation at high purity has limited their utility.

Recently, the potential value of nisin for the milk industry has been recognized, in particular, in connection with the ability of nisin to help fight mastitis infection in cows. The advantage offered by nisin stems, in large part, from its potential to reduce or eliminate "withhold period" rules. The withhold period is a time established, during treatment of mastitis infection of cows, when milk from the infected cow must be discarded. Thus, milk from cows treated with nisin for mastitis infection can enter the fluid milk stream immediately compared to traditional antibiotic treatment.

Unfortunately, nisin that is commercially produced by currently available methods of production and purification is considered food grade quality and is not of sufficient purity for pharmaceutical applications. Currently available methods use media comprising whey protein concentrate (WPC) during fermentation of lantibiotic-producing microorganisms to produce lantibiotics. However, the concentrations of WPC necessary for efficient production of lantibiotics using methods normally used to prepare lantibiotics lead to the production of drug substance impurities. Therefore, due to the lack of efficient alternative methods of production and purification which could produce nisin free of such impurities, the value derived from treatment of mastitis with nisin is insufficient to counterbalance current practices.

There is a long-felt need for improved, cost-effective, commercially-viable, culture methods for lantibiotic production without also producing contaminating high levels of WPC-related impurities in the initial preparation. Such culture methods can yield lantibiotics having high purity suitable for pharmaceutical use.

SUMMARY OF THE INVENTION

This section will be completed upon finalizing the claims.

DETAILED DESCRIPTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention is based on the inventors' surprising discovery of culture media, methods of preparing culture media, culture conditions, and culture methods capable of producing pharmaceutical grade preparations of lantibiotics that are substantially free of impurities. More specifically, the inventors discovered that pharmaceutical grade lantibiotics can be efficiently and cost-effectively produced when lantibiotic-producing microorganisms are cultured in media comprising reduced concentrations of whey protein concentrate (WPC) and that has been subjected to high shear conditions to fully wet and disperse the WPC. The media further comprises carefully selected concentrations of protease. Most notably, culture conditions and methods of the invention can produce pharmaceutical grade lantibiotic compositions that are substantially free of aggregates and whey protein-derived impurities referred to as the "34 min" impurities and identified as α-lactalbumin and β-lactoglobulin oligomers. Importantly, when compared to currently used culture methods for producing lantibiotics, the use of the instant culture media, conditions, and culture methods can be used to produce pharmaceutical grade lantibiotic compositions that are substantially free of impurities without affecting the yield of the lantibiotic.

I. Method of Producing

In one aspect, the present invention provides culture methods for producing pharmaceutical grade preparations of a lantibiotic that are substantially free of impurities. A method of the instant invention comprises providing a WPC-based culture medium comprising whey proteins at a concentration of about 10 g/L or below. The WPC in the medium is fully wetted and dispersed by subjecting the media to high shear conditions. The culture medium is then inoculated with a microorganism capable of producing a lantibiotic. The inoculated medium is fermented under conditions favorable for the growth and/or metabolic activity of the lantibiotic-producing microorganism for a period of time sufficient to produce a fermentation broth comprising the lantibiotic. The method further comprises subjecting the culture medium to protease treatment under conditions which result in selective proteolytic activity against protein or polypeptide impurities in the culture medium, without measurable proteolysis of the lantibiotic. The method may further comprise purifying the lantibiotic to produce the pharmaceutical grade composition comprising the lantibiotic.

A. Lantibiotics

Lantibiotics are a class of peptide antibiotics that contain the characteristic polycyclic thioether amino acids lanthionine or methyllanthionine, as well as the unsaturated amino acids dehydroalanine and 2-aminoisobutyric acid. Lantibiotics are produced by a large number of Gram-positive bacteria such as *Streptococcus* and *Streptomyces* to attack other Gram-positive bacteria, and as such, they are considered a member of the bacteriocins. Bacteriocins are classified according to their extent of posttranslational modification. The lantibiotics are a class of more extensively modified bacteriocins, also called Class I bacteriocins.

Methods of the instant invention may be used to produce preparations of bacteriocins that are substantially free of impurities. Preferably, the bacteriocins are lantibiotics. Non-limiting examples of lantibiotics that may be produced using methods of the instant invention include type A lantibiotics such as nisin, bisin, subtilin, epidermin, gallidermin, mutacin II, mutacin I, and mutacin III, type B lantibiotics such as mersacidin, actagardine, duramycin, cinnamycin, and haloduracin. Preferably, methods are used to produce nisin, more preferably nisin A.

B. Nutrient Media

As stated herein, the first step of the process comprises providing a culture medium. The term "culture medium" is used herein to refer to media in the form originally provided for fermentation. The culture medium supplies the substrates and the nutrients a microorganism needs to grow and to produce the various fermentation products. The culture medium typically used to produce lantibiotics is an aqueous medium comprising a fermentable substrate, a nitrogen source, and optionally micronutrients, wherein the microorganism can grow and reproduce. Non-limiting examples of a nitrogen source include plant derived protein such as soy protein and pea protein, dairy protein, yeast or yeast extract, meat extract, various kinds of fermentation fungi, as well as hydrolysates of any of the aforementioned proteins.

i. Whey Protein Concentrate

Preferably, the nitrogen source is derived from a dairy product. As used herein, the term "dairy product" refers to whole (animal) milk, components of the milk as well as products derived from milk, such as whey, whey permeate, milk permeate, yoghurt and quark and by-products from the preparation of yoghurt and quark. More preferably, the nitrogen source is whey-based. Preferably, the whey protein concentrate is a dry whey protein concentrate (WPC) composition. The concentration of WPC in a culture medium of the invention can and will vary depending on the concentration of whey proteins in the WPC used. A most preferred WPC is a WPC comprising about 70% whey proteins or above, preferably comprising about 80% whey proteins (WPC80).

In some embodiments, a culture medium may further comprise yeast extract as a nitrogen source. For instance, a culture medium may further comprise yeast extract at a concentration ranging from about 1 g/L to about 10 g/L, preferably from about 3 g/L to about 7 g/L.

In methods normally used to prepare lantibiotics, WPC is added to the medium to provide whey proteins at a concentration of about 20 to about 30 g/L. However, as it was described above, a culture medium of the instant invention comprises whey protein at concentrations substantially lower than the concentrations normally used in nutrient media for producing lantibiotics. A culture medium of the instant disclosure comprises whey protein from WPC in an amount sufficient to provide whey proteins at a concentration of about 15 g/L or below, about 10 g/L or below, more preferably at a concentration of about 7 g/L to about 9 g/L.

In preferred embodiments, a culture medium of the instant disclosure comprises whey protein from WPC in an amount sufficient to provide whey proteins at a concentration of about 8 g/L.

When the WPC used to prepare the medium normally used for producing lantibiotics is WPC comprising about 80% whey proteins (WPC80), 32.5 g of the WPC80 is added to 1 L nutrient media. Conversely, when the WPC used to prepare the culture medium of the instant invention is WPC80, about 9.75 g of the WPC is added to 1 L nutrient media. Individuals of skill in the art will recognize that concentrations of WPC other than WPC80 may be calculated to provide a desired concentration of whey proteins in the medium.

ii. Fermentable Substrate

A fermentable substrate refers to the carbon source that is converted into another compound by the metabolic action of microorganisms. As a carbon source, mono-, di-, tri-, oligo and polysaccharides may be used, in particular sugars such as glucose, sucrose, fructose, galactose and lactose, and/or starch (hydrolysates). These carbohydrates can be derived from a variety of sources, such as dairy products and plant, fruit or vegetable-derived products, e.g., molasses, fruit or vegetable juices, fruit or vegetable pulp, etc. The invention can be practiced using one or more carbohydrates in partly or substantially purified form. Alternatively, the invention can be practiced using a raw material containing one or more carbohydrates. Preferably, in this invention, the substrate is a carbohydrate selected from the group consisting of lactose, sucrose, glucose, and combinations thereof, most preferably lactose. The culture medium typically comprises 5-300 g/L, 10-100 g/L, or 20-70 g/L, and preferably 30-60 g/L of the carbohydrate.

In some embodiments of the invention, the culture medium further comprises micronutrients that support the growth and metabolic action of the lantibiotic-producing microorganism, such as vitamins, minerals, co-factors and/or other trace elements. Micronutrients are generally used at a rate of at least 0.01% (w/v), preferably at a rate of between 0.1 and 2% (w/v) in the culture medium. In some instances, the carbohydrate sources and/or nitrogen sources that may be used in accordance with the invention inherently contain micronutrients. Preferably, micronutrients of a culture medium comprise calcium chloride, magnesium sulfate, and sodium chloride. The concentration of calcium chloride may range from about 0.01 g/L to about 10 g/L, from about 0.1 g/L to about 5 g/L, preferably from about 0.4 to about 0.6 g/L. The concentration of magnesium sulfate may range from about 0.01 g/L to about 10 g/L, from about 0.1 g/L to about 3 g/L, preferably from about 0.2 to about 0.4 g/L. The concentration of sodium chloride may range from about 0.001 g/L to about 1 g/L, from about 0.01 g/L to about 0.02 g/L, preferably from about 0.013 to about 0.018 g/L The pH of a culture medium may range from about 2 to about 9. Preferably, the pH of a culture medium ranges from about 5.5 to about 7.5. More preferably, the pH of a culture medium ranges from about 6 to about 6.4. Methods of adjusting the pH of a nutrient medium are known in the art, and may comprise the addition of a pH modifier.

iii. Media Preparation

Generally, a culture medium of the instant invention is prepared by combining a WPC with the ingredients of the culture medium described above. As it is normally practiced in the art, a culture medium may be prepared in a fermenter and agitated using the agitator of a fermenter to wet and disperse ingredients of a culture medium. A culture medium of the invention is further subjected to high shear conditions to fully disperse the WPC in the medium to produce a culture medium. As used herein, the terms "fully disperse" and "fully wet" may be used interchangeably and refer to a visual evaluation of the complete dispersal of the WPC in the medium. For instance, visual evaluation of the complete dispersal of the WPC in the medium may comprise the visual confirmation of the absence of clumping (fisheyes) of WPC in the medium.

Methods of subjecting a medium to mechanical shear conditions are well known in the art and may include the use of scraped-surface heat-exchangers or homogenizers, or by using shear mixers. Preferably, the medium is subjected to mechanical shear conditions using a high shear mixer to fully disperse WPC in the medium. A high shear mixer disperses, or transports, one phase or ingredient (liquid, solid, gas) into a main continuous phase (liquid), with which it would normally be immiscible. A rotor or impeller, together with a stationary component known as a stator, or an array of rotors and stators, is used either in a tank containing the solution to be mixed, or in a pipe through which the solution passes, to create shear.

Non-limiting examples of high shear mixers that may be used in the instant invention include batch high-shear mixers, inline high-shear mixers, inline powder induction mixers, and combinations thereof. Preferably, the medium is subjected to mechanical shear using a batch powder induction and dispersion system. A shear mixer may be capable of producing a liquid flow ranging from about 10 gpm to about 90 gpm and a vacuum ranging from about 5 Hg to about 30 Hg. High shear conditions may range from about 10,000 to 500,000 s-1 of shear. In some methods, the medium is typically sheared by a high-shear mixer or colloid mill, at a temperature of about 90 to 300° F. for about 0.01 to 0.5 seconds.

When the medium is subjected to mechanical shear using a batch powder induction and dispersion system, the medium is subjected to a single cycle through the shear pump. Alternatively, the medium is subjected to multiple cycles. Preferably, the medium is subjected to a sufficient number of cycles to fully disperse WPC in the medium.

C. Microorganism

The method further comprises inoculating the medium with a microorganism capable of producing lantibiotics. Preferably the microorganism is capable of producing nisin. Non-limiting examples of microorganisms capable of producing lantibiotics include Gram-positive bacteria such as *Lactobacillus, Streptococcus*, and *Streptomyces*. Preferably, the medium is inoculated with a "lactic acid bacteria" capable of producing nisin. In some embodiments, the fermentation broth comprises a single isolate of lantibiotic-producing microorganisms. In other embodiments, the fermentation broth comprises a mixture of lantibiotic-producing microorganisms, at least one of which is capable of producing a lantibiotic. In some preferred embodiments, the lantibiotic-producing microorganism belongs to the order Lactobacillales, preferably to the *Lactococcus* genus. The lantibiotic-producing microorganism most preferably belongs to *Lactococcus lactis* ssp. *lactis*, and examples thereof include JCM 7638, ATCC 11454, NCDO 497, 880D, and IFO 12007. Preferably, the lantibiotic-producing microorganism produces nisin, and is derived from *Lactococcus lactis* ssp. *lactis* strain 880D.

In accordance with fermentation methods using lantibiotic-producing microorganisms, the medium may be inoculated with a broth containing a lantibiotic-producing microorganism. The term 'activated' may be used herein to indicate that the composition used to inoculate a culture medium comprises a lantibiotic-producing microorganism in a metabolically active state. When the microorganisms are introduced into the culture medium during direct seeding, i.e., in the form of a dry, liquid or frozen concentrate, the lantibiotic-producing microorganisms do not take effect straight away and require time to become active. This "time lag", also referred to as "lag phase", may involve re-establishment of the stored bacteria into the natural form (rehydration phase of the bacteria), restoration of the metabolic activity, and/or adaptation to the new environment.

D. Protease Treatment

As stated herein, a method further comprises subjecting the culture medium to protease treatment. Subjecting the culture medium to protease treatment is performed using carefully selected concentrations of protease which result in selective proteolytic activity against protein or polypeptide impurities in the culture medium, without measurable proteolysis of the lantibiotic.

In essence, the protease treatment comprises adding a protease to the medium and incubating the medium under conditions suitable for protease digestion. Protease may be added to the medium at any step in a method of the invention. For instance, protease may be added during preparation of the medium, at the time of inoculation of the medium with a microorganism capable of producing the lantibiotic, during fermentation of the inoculated medium, after fermentation of the inoculated medium, or a combination thereof. Preferably, protease is added to a medium during preparation of the medium. Adding protease to a medium during preparation of the medium may allow for proteolytic activity to occur during preparation of the medium, and to continue through fermentation.

Proteases suitable for use in a method of the invention may be any protease capable of selective proteolytic activity against protein or polypeptide impurities in the culture medium, without measurable proteolysis of the lantibiotic. Non-limiting examples of proteases include trypsin, endopeptidase Arg-C, thermolysin, S8 protease, subtilisin, proteinase K, pepsin, papain, clostripain, lysyl endopeptidase, endopeptidase Asp-N, enterokinase, or Factor Xa. Preferably, a protease suitable for use in a method of producing lantibiotics is an S8 serine endopeptidase, more preferably subtilisin. An exemplary subtilisin may be a formulation of subtilisin sold under the brand name of Alcalase®.

In methods normally used to prepare lantibiotics, protease is added to the medium to provide 1.4 units of protease in 1 L of media. However, a culture medium of the instant invention comprises protease at concentrations substantially lower than the concentrations normally used in nutrient media for producing lantibiotics. A culture medium of the instant disclosure comprises protease at about 50%, 40%, or about 30% or lower of the concentration normally used in culture media. As such, a culture medium of the instant disclosure comprises protease at a concentration of about 0.7 U/L, 0.56 U/L, or about 0.5 U/L or lower. In preferred embodiments, a culture medium of the instant disclosure comprises protease at a concentration of about 0.5 U/L or lower.

Following completion of proteolytic digestion, it may be desirable to remove the protease. A particularly convenient method for facilitating removal of the protease following digestion is to provide the protease attached to a solid support (e.g., an agarose or a magnetic bead). In this format, the solid support is easily separated from the incubation mixture following digestion. Alternatively, simple sizing column steps may be employed to effect removal of the protease. Other techniques for removing proteases following proteolytic digestions are known in the art, including chromatography techniques such as those based on affinity, ion exchange, and hydrophobicity.

It should be noted that although it may be desirable to remove the proteases after the impurities have been digested, it is not necessary to do so for all applications. For example, if the purified lantibiotic is intended to be consumed with a food product, the protease may not have to be removed in order to satisfy relevant regulations.

E. Fermentation

As stated herein, a method of the invention comprises fermenting the inoculated culture medium. Fermenting the inoculated culture medium comprises incubating the inoculated medium under conditions favorable to the growth and/or metabolic activity of the lantibiotic-producing microorganism for a period of time sufficient to produce a fermentation broth comprising the lantibiotic. While not wishing to be bound by theory, it is believed that the media conditions favorable to metabolic biosynthesis and export of lantibiotics are also conditions which result in selective proteolytic activity against protein or polypeptide impurities in the culture medium and fermentation broth, without measurable proteolysis of the lantibiotic.

Conditions favorable to the growth and/or metabolic activity of microorganisms are well known in the art and may include the use of sterile conditions and agitation in a bioreactor at a temperature ideal for growth of the microorganism. In some preferred embodiments, the inoculated medium is incubated at a temperature between 32° C. and 43° C.

Duration of fermentation can and will vary depending on the microorganism, the culture media, and the lantibiotic to be produced, among other variables. In general, fermentation is performed for a duration of time to produce a viable quantity of a lantibiotic. Under the conditions described herein, fermentation may be performed for a duration typically varying between 10-30 hours, although the invention is not particularly limited in this respect. In some embodiments, fermentation conditions comprise incubation at a temperature ranging from about 30° C. to about 34° C., for 18-24 hr, without aeration.

As it will be recognized, after the duration of fermentation, a lantibiotic-producing microorganism in the fermentation broth may be inactivated using methods known in the art. Similarly, and as described above, after the duration of fermentation, the protease in the fermentation broth may be inactivated using methods known in the art.

F. Lantibiotic Production and Purification

Importantly, although methods of the instant invention comprise use of a culture medium comprising whey protein at concentrations substantially lower than concentrations normally used for producing lantibiotics, the methods produce a lantibiotic preparation that is substantially free of impurities without affecting the yield of the lantibiotic when compared to lantibiotic yields produced using conventional methods (e.g., when WPC is added to the medium to provide whey proteins at a concentration of about 20 to about 30 g/L). Methods of the invention may produce fermentation broth comprising lantibiotic at a concentration ranging from about 40 mg/L to about 200 mg/L, or about 40 mg/L to about 150 mg/L.

A lantibiotic produced using methods of the invention may be further purified to produce a pharmaceutical grade composition comprising a lantibiotic of sufficient purity for pharmaceutical applications. Methods of purifying peptides such as lantibiotics are generally known in the art. For general guidance in suitable purification techniques, see Scopes, R., Protein Purification, Springer-Vertag, NY (1982). In general, peptides may be purified via standard methods including electrophoretic, molecular, immunological and chromatographic techniques, filtration such as ultrafiltration, diafiltration, and microfiltration, ion exchange, hydrophobic, affinity, and reverse-phase HPLC chromatography, chromatofocusing, and combinations thereof.

Using any of the purification methods known in the art, a lantibiotic may be purified by removing from the fermentation broth any undesirable ingredient of the culture medium and/or any product of fermentation other than the lantibiotic of interest. Alternatively, a lantibiotic may be purified by selectively isolating the lantibiotic. Additionally, a lantibiotic may be purified by removing products of fermentation and by selectively isolating the lantibiotic. A lantibiotic may further be concentrated using methods known in the art.

When methods of the invention are used to produce lantibiotics, further purifying the lantibiotics produces a pharmaceutical grade composition of lantibiotics having levels of drug substance impurities that are lower than the levels of drug substance impurities produced by methods normally used to produce lantibiotics. Levels of drug substance impurities in the pharmaceutical grade composition may be lower than the levels of drug substance impurities produced by methods normally used to produce lantibiotics by about 30%, 40%, 50%, 60%, or about 70% or more. A pharmaceutical grade composition of lantibiotics generally comprises lantibiotics having a purity at or about 90%, 95%, 99%, or higher, preferably above 95%.

The pharmaceutical grade compositions of lantibiotics comprise no more than 5%, 4%, 3%, or 2% drug substance impurities. Additionally, a pharmaceutical grade composition of lantibiotics comprises less than 1% of the "34 min" α-lactalbumin and β-lactoglobulin oligomer impurities. Preferably, a pharmaceutical grade composition of lantibiotics comprises undetectable levels of the α-lactalbumin and β-lactoglobulin oligomer impurities.

A lantibiotic may be purified and/or concentrated to provide a pharmaceutical grade drug product comprising a concentration of lantibiotics ranging from about 1 g/L to about 20 g/L, about 1 g/L to about 10 g/L, preferably about 3 g/L to about 10 g/L, more preferably about 5 g/L to about 7 g/L.

II. Microbial Culture Medium

In another aspect, the present invention provides a microbial culture medium for producing pharmaceutical grade lantibiotic compositions. The microbial culture medium comprises a solution of a fermentable substrate, micronutrients, and whey protein concentrate in an amount sufficient to provide whey proteins at a concentration of about 15 g/L or below, about 10 g/L or below, more preferably at a concentration of about 8 g/L or below. The whey protein concentrate is fully dispersed in the culture medium. The culture medium further comprises a protease. When the protease is subtilisin, the concentration of subtilisin in the media may be about 0.5 U/L or lower. The culture medium and use of the culture medium for producing pharmaceutical grade lantibiotic compositions are described in Section I above.

III. Production System

In yet another aspect, the present invention provides a system for producing a pharmaceutical grade lantibiotic composition. The system comprises a bioreactor for fermenting a microbial growth medium comprising a WPC and a powder induction and dispersion system capable of producing high shear conditions. The powder induction and dispersion system is operatively disposed to dispense the WPC into a stream of liquid microbial growth medium circulating between the fermenter and the powder induction and dispersion system. The powder induction and dispersion system is also capable of fully hydrating and dispersing the WPC, thereby allowing the use of WPC at concentrations significantly lower than the concentrations normally used in fermentation media for producing lantibiotics. Preferably, the powder induction and dispersion system is a FastFeed-425® high shear device from Admix.

IV. Lantibiotic Compositions

In yet another aspect, the present invention provides compositions comprising lantibiotics. In some embodiments, a composition may comprise a fermentation broth comprising lantibiotics. As described above, lantibiotics commercially produced by currently available methods of production and purification are not of sufficient purity for pharmaceutical applications. Conversely, culture conditions and methods of the invention produce pharmaceutical grade lantibiotic compositions substantially free of whey protein-derived impurities, especially the "34 min" impurities identified as α-lactalbumin, β-lactoglobulin oligomers, and aggregates. Importantly, although methods of the instant invention comprise use of a culture medium comprising whey protein at concentrations substantially lower than concentrations normally used for producing lantibiotics, the methods produce a lantibiotic preparation that is substantially free of impurities without affecting the yield of the lantibiotic when compared to lantibiotic yields produced using conventional methods.

A composition may comprise purified lantibiotic compositions comprising pharmaceutical grade lantibiotics. The pharmaceutical grade lantibiotics may be as described in Section 1(F).

Definitions

Unless defined otherwise, all technical and scientific terms used herein have the same meaning as is commonly understood by one of ordinary skill in the art. All patents, applications, published applications, and other publications are incorporated by reference in their entirety. In the event that there is a plurality of definitions for a term herein, those in this section prevail unless stated otherwise.

As used herein, the term 'fermentation broth' is used to refer to the culture medium after inoculation with a microorganism. Thus, strictly speaking, several types of "fermentation broths" can be distinguished based on the stage to which the fermentation has progressed: (i) nutrient media in the form originally provided including microorganisms directly after inoculation; (ii) nutrient media undergoing fermentation wherein some or most of the originally provided nutrients have already been consumed and fermentation products including lactate have been excreted into the media by the microorganisms; and, (iii) media that have been removed from the fermentor after part or all of the nutrients have been consumed.

As used herein, the term "fermentable substrate" refers to the carbon source that is converted into another compound by the metabolic action of microorganisms. As a carbon source, mono-, di-, tri-, oligo and polysaccharides may be used, in particular sugars such as glucose, sucrose, fructose, galactose, and lactose and/or starch (hydrolysates).

As used herein, the term "lantibiotic" is any polypeptide having the structural features described above. Thus, while the Exemplification section focuses primarily on the lantibiotic nisin, the principles established herein would be expected to apply to all lantibiotics due to the presence of their defining structural characteristics. Other lantibiotics include, for example, subtilin, epidermin, gallidermin, mutacin, pep5, epicidin, epilancin, lacticin, cytolysin, staphylococci n, salvaricin, lactocin, streptococcin, sublancin, carnocin, variacin, cypemycin, connamycin, duramycin, ancovenin, mersacidin, and actagurdine.

As used herein, the term "pharmaceutical grade" refers to a composition of lantibiotics having levels of drug substance impurities that are lower than the levels of drug substance impurities produced by methods normally used to produce lantibiotics by about 30%, 40%, 50%, 60%, or about 70% or more. A pharmaceutical grade composition of lantibiotics generally comprises lantibiotics having a purity at or about 90%, 95%, 99%, or higher, preferably above 95%, and comprises no more than 4%, 3%, or 2% drug substance impurities. Additionally, a pharmaceutical grade composition of lantibiotics comprises less than 1% or undetectable levels of the "34 min" impurities.

Examples

The following examples are included to demonstrate the disclosure. It should be appreciated by those of skill in the art that the techniques disclosed in the following examples represent techniques discovered by the inventors to function well in the practice of the disclosure. Those of skill in the art would, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: Use of Powder Induction System and Reduction in WPC80/Alcalase for the Improvement of Nisin Purity

*L. lactis* growth media for the production of nisin drug substance has historically been prepared using WPC80 and other media constituents. For 1000 L fermentation scale, 32.5 kg (100%) WPC80 is added to a fermentation vessel, and the vessel's agitator is utilized to mix the WPC80 into solution. Following this, an enzymatic solution comprising alcalase is added at 0.5 L (100%), followed by other media components and eventual media sterilization. However, two undesirable issues were encountered with this approach: 1) mixing of WPC80 using the fermenter's agitation blades led to incomplete mixing, visible clumping ("fisheyes") and a non-homogeneous media preparation, and 2) addition of WPC80 and alcalase at 100% concentration led to higher drug substance impurities; most notably, a WPC80-derived impurity referred to as the "34 min" impurity and identified as α-lactalbumin, β-lactoglobulin oligomers, and aggregates.

As an alternative to using agitation for media preparation, the utilization of the Admix FastFeed-425 high shear device was introduced into the process. This system, comprised of two pumps, draws water from the fermenter vessel into the device and recirculates the water back to the vessel, thereby creating a vacuum. Upon addition of the WPC80, the vacuum draws the WPC80 into the recirculating water stream and passes the WPC80 through a high shear pump onward to the fermenter. By recirculation between the device and fermenter, the WPC80 is completely "wetted out" and fully re-suspended, leaving no visible clumping.

While the issue of incomplete media preparation was resolved, the reduction in overall drug substance impurity levels was not realized until manipulation of both the levels of WPC80 and alcalase were performed. Using both components at 100% resulted in unacceptable levels of the 34 min impurity, contributing to overall higher drug substance impurities (Table 1).

C12 HPLC analysis is used to analyze concentration, impurities, and overall quality of nisin of in-process samples and final drug substance. At 100% of both WPC80 and alcalase, there were significant impurities present in drug substance when the fermenter's agitation blades were used to prepare media. The same result occurred when the induction system was used to prepare the media (lot 68306) indicative of other contributing factors leading to unacceptable impurities.

Knowing the 34 min impurity was WPC80-derived, it was suggested that reducing the quantity of WPC80 during media preparation may be beneficial to reducing impurities. Subsequent production runs were conducted whereby the WPC80 and alcalase were incrementally decreased until both media components were reduced to 30%. At this level, L. lactis growth and nisin production were still achievable and a significant reduction in total and 34 min impurities was observed in drug substance.

Overall, the combination of implementing the induction system while carefully titrating down the WPC80 and alcalase levels resulted in producing nisin yields ranging from about 40 mg/L to about 150 mg/L in the fermentation broth, at or about 100% of optimal Nisin yields.

Nisin A was further purified to produce a pharmaceutical grade composition comprising nisin A at a concentration of about 5 g/L to about 7 g/L. Additionally, the combination of culture methods and purification resulted in the elimination of the highly undesirable 34 min impurity and a purity of about 95% or higher.

TABLE 1

Media Preparation Modification and Effects of Reducing Drug Substance Impurities.

| Production Lot | % WPC80 (w/v) | % alcalase (v/v) | % Drug Substance Impurity[1] (total) | % Drug Substance Impurity[1] (34 min) | WPC80 Media Mixing Equipment | Quality of Prepared Media |
|---|---|---|---|---|---|---|
| 65210 | 100 | 100 | 6.25 | 2.20 | Fermenter agitator | Visible clumps/non-homogeneous |
| 66252 | 100 | 100 | 4.29 | 2.20 | Fermenter agitator | Visible clumps/non-homogeneous |
| 67417 | 100 | 100 | 5.90 | 5.71 | Fermenter agitator | Visible clumps/non-homogeneous |
| 68306 | 100 | 100 | 6.03 | 5.11 | Admix FF-425 induction | Completely soluble/homogeneous |
| 69319 | 30 | 30 | 2.15 | 0.00 | Admix FF-425 induction | Completely soluble/homogeneous |
| 69446 | 30 | 30 | 3.16 | 0.00 | Admix FF-425 induction | Completely soluble/homogeneous |
| 69488 | 30 | 30 | 3.36 | 0.00 | Admix FF-425 induction | Completely soluble/homogeneous |

What is claimed is:

1. A method of producing a pharmaceutical grade lantibiotic composition, the method comprising:
    a. providing a whey protein concentrate (WPC)-based culture medium comprising whey proteins at a concentration of about 10 g/L or below;
    b. fully wetting and dispersing the WPC in the culture medium;
    c. inoculating the culture medium with a microorganism belonging to the *Lactococcus* genus and capable of producing the lantibiotic to produce an inoculated medium;
    d. fermenting the inoculated medium under conditions favorable to growth and/or metabolic activity of the microorganism, for a period of time sufficient to produce a fermentation broth comprising the lantibiotic;
    e. subjecting the culture medium to treatment with a protease at any of steps a, b, c, and d, and combinations thereof; and
    f. purifying the lantibiotic to produce a pharmaceutical grade composition comprising the lantibiotic.

2. The method of claim 1, wherein the WPC-based culture medium comprises whey proteins at a concentration of about 7 g/L to about 9 g/L.

3. The method of claim 1, wherein the WPC comprises 80% w/w whey proteins.

4. The method of claim 1, wherein the WPC is fully wetted and dispersed in the medium by subjecting the WPC-based medium to high shear conditions.

5. The method of claim 4, wherein the WPC is fully wetted and dispersed by subjecting the culture medium to high shear conditions using a batch powder induction and dispersion system.

6. The method of claim 1, wherein the culture medium is subjected to protease treatment at steps a-c.

7. The method of claim 1, wherein the protease is an S8 serine endopeptidase.

8. The method of claim 1, wherein the protease is subtilisin.

9. The method of claim 8, wherein the concentration of subtilisin in the media is about 0.5 U/L or lower.

10. The method of claim 1, wherein the concentration of lantibiotic in the fermentation broth ranges from about 40 mg/L to about 150 mg/L.

11. The method of claim 1, wherein the lantibiotic is nisin A.

12. The method of claim 1, wherein the pharmaceutical grade composition comprises lantibiotics having a purity of about 95% or higher.

13. The method of claim 1, wherein the pharmaceutical grade composition comprises undetectable levels of α-lactalbumin oligomer, β-lactoglobulin oligomer, aggregates, and combinations thereof.

14. The method of claim 1, wherein the pharmaceutical grade composition of lantibiotics comprises no more than about 5% drug substance impurities.

15. The method of claim 1, wherein the pharmaceutical grade composition comprises lantibiotic at a concentration of about 5 g/L to about 7 g/L.

16. The method of claim 1, wherein fermentation comprises incubation at a temperature ranging from about 30° C. to about 34° C., for 18-24 hr.

17. A method of producing a pharmaceutical grade lantibiotic composition, the method comprising:
   a. providing a whey protein concentrate (WPC)-based culture medium comprising whey proteins at a concentration of about 10 g/L or below;
   b. subjecting the culture medium to high shear conditions to fully wet and disperse the WPC in the culture medium;
   c. inoculating the culture medium with a microorganism belonging to the *Lactococcus* genus and capable of producing the lantibiotic to produce an inoculated medium;
   d. fermenting the inoculated medium at a temperature ranging from about 30° C. to about 34° C., for 18-24 hr to produce a fermentation broth comprising the lantibiotic;
   e. subjecting the culture medium to treatment with a protease at any of steps a, b, c, and d, and combinations thereof; and
   f. purifying the lantibiotic to produce a pharmaceutical grade composition comprising the lantibiotic;
   wherein the protease is subtilisin, and the concentration of subtilisin in the media is about 0.5 U/L or lower.

18. A microbial culture medium for producing a pharmaceutical grade lantibiotic composition, the culture medium comprising:
   a. a WPC-based culture medium comprising whey proteins at a concentration of about 10 g/L or below;
   b. fermentable substrate;
   c. micronutrients; and
   d. an S8 serine endopeptidase; and
   wherein the WPC in the culture medium is fully wetted and dispersed.

19. The microbial culture medium of claim 18, wherein the S8 serine endopeptidase is subtilisin, and the concentration of subtilisin in the media is about 0.5 U/L or lower.

20. The microbial culture medium of claim 19, further comprising a microorganism capable of producing a lantibiotic.

21. The microbial culture medium of claim 18, wherein the WPC in the culture medium is fully wetted and dispersed by subjecting the culture medium to high shear conditions.

* * * * *